United States Patent [19]

Matsuo et al.

[11] Patent Number: 5,670,533

[45] Date of Patent: Sep. 23, 1997

[54] PYRAZOLE DERIVATIVES, PROCESSES FOR PREPARATION THEREOF AND PHARMACEUTICAL COMPOSITION COMPRISING THE SAME

[75] Inventors: Masaaki Matsuo, Toyonaka; Kiyoshi Tsuji, Kishiwada; Takashi Ogino, Yamatokooriyama; Nobukiyo Konishi, Nagaokakyo, all of Japan

[73] Assignee: Fujisawa Pharmaceutical Co., Ltd., Osaka, Japan

[21] Appl. No.: 579,974

[22] Filed: Dec. 28, 1995

Related U.S. Application Data

[63] Continuation of Ser. No. 413,939, Mar. 30, 1995, Pat. No. 5,550,147, which is a continuation of Ser. No. 297, Jan. 4, 1993, abandoned.

[30] Foreign Application Priority Data

| Feb. 5, 1992 | [GB] | United Kingdom | 9202442 |
| Sep. 28, 1992 | [GB] | United Kingdom | 9220427 |

[51] Int. Cl.$^6$ .................. A61K 31/495; C07D 231/10
[52] U.S. Cl. .................. 514/106; 548/375.1; 548/376.1
[58] Field of Search .................. 548/375.1, 376.1; 514/406

[56] References Cited

U.S. PATENT DOCUMENTS 5,134,142  7/1992  Matsuo et al. .

*Primary Examiner*—Robert Gerstl
*Attorney, Agent, or Firm*—Oblon, Spivak, McClelland, Maier & Neustadt, P.C.

[57] ABSTRACT

The present invention relates to new pyrazole derivatives represented by the following general formula (I)

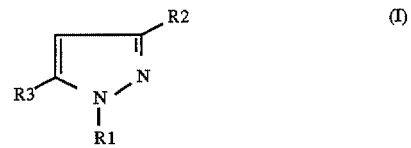

wherein $R^1$ is aryl which is substituted with substituent(s) selected from the group consisting of lower alkylthio, cyclo(lower)alkyl, hydroxy, hydroxy(lower) alkyl, cyano, lower alkylenedioxy, acyl, acyloxy, aryloxy and lower alkoxy optionally substituted with acyl or lower alkoxy, $R^2$ is halogen, halo(lower)alkyl, cyano or acyl, and $R^3$ is aryl substituted with nitro, hydroxy, lower alkoxy, lower alkylthio, lower alkylsulfinyl or lower alkylsulfonyl, provided that when $R^3$ is aryl substituted with nitro, hydroxy or lower alkoxy, then $R^1$ is aryl substituted with lower alkylthio, lower alkylsulfinyl or lower alkylsulfonyl, and pharmaceutically acceptable salts thereof.

4 Claims, No Drawings

PYRAZOLE DERIVATIVES, PROCESSES FOR PREPARATION THEREOF AND PHARMACEUTICAL COMPOSITION COMPRISING THE SAME

This is a continuation of application Ser. No 08/413,939 filed on Mar. 30, 1995, now U.S. Pat. No. 5,550,447, which is a continuation of Ser. No. 08/000,297 filed on Jan. 4, 1993, now abandoned.

The present invention relates to new pyrazole derivatives and pharmaceutically acceptable salts thereof.

More particularly, it relates to new pyrazole derivatives and pharmaceutically acceptable salts thereof, which have antiinflammatory, analgesic and antithrombotic activities, to processes for preparation thereof, to a pharmaceutical composition comprising the same, and to methods of using the same therapeutically in the treatment and/or prevention of inflammatory conditions, various pains, collagen diseases, autoimmune diseases, various immunity diseases and thrombosis in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis, etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atropic gastritis, gastritis varialoforme, ulcerative coliris, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lupus erythematosus, scleroderma, polymyositis, periarteritis nodosa, rheumatic fever, Sjögren's syndrome, Behcet disease, thyroidiris, type I diabetes, nephrotic syndrome, aplastic anemia, myasthenia gravis, uveitis contact dermatitis, psoriasis, Kawasaki disease, sarcoidosis, Hodgkin's disease, and the like. Additionally, the object compound is expected to be useful as therapeutical and/or preventive agents for cardiovascular or cerebrovascular diseases, the diseases caused by hyperglycemia and hyperlipemia.

One object of this invention is to provide new and useful pyrazole derivatives and pharmaceutically acceptable salts thereof, which possess antiinflammatory, analgesic and antithrombotic activities.

Another object of this invention is to provide processes for the preparation of said pyrazole derivatives and salts thereof.

A further object of this invention is to provide a pharmaceutical composition comprising, as an active ingredient, said pyrazole derivatives and pharmaceutically acceptable salts thereof.

Still further object of this invention is to provide a therapeutical method for the treatment and/or prevention of inflammatory conditions, various pains, and the other diseases mentioned above, using said pyrazole derivatives and pharmaceutically acceptable salts thereof.

Some pyrazole derivatives having antiinflammatory and analgesic activities have been known as described, for example, in Canadian Patent 1 130 808, and EP Patent publication Nos. 272 704, 293 220 and 418 845.

The object pyrazole derivatives of this invention are new and can be represented by the following general formula [I].

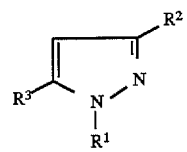

wherein
$R^1$ is aryl which is substituted with substituent(s) selected from the group consisting of lower alkylthio, cyclo (lower)alkyl, hydroxy, hydroxy(lower)alkyl, cyano, lower alkylenedioxy, acyl, acyloxy, aryloxy and lower alkoxy optionally substituted with acyl or lower alkoxy, $R^2$ is halogen, halo(lower)alkyl, cyano or acyl, and $R^3$ is aryl substituted with nitro, hydroxy, lower alkoxy, lower alkylthio, lower alkylsulfinyl or lower alkylsulfonyl, provided that when $R^3$ is aryl substituted with nitro, hydroxy or lower alkoxy,
  then $R^1$ is aryl substituted with lower alkylthio, lower alkylsulfinyl or lower alkylsulfonyl, and pharmaceutically acceptable salts thereof.

The object compound [I] or its salt can be prepared by the following processes.

Process 1

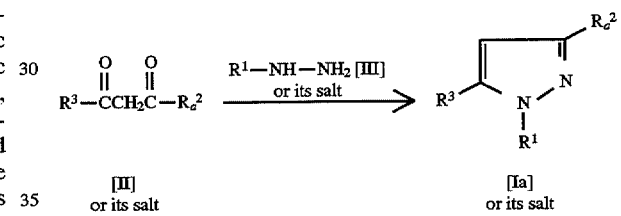

Process 2

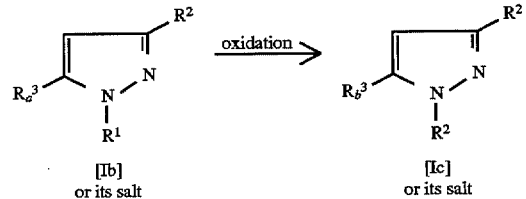

Process 3

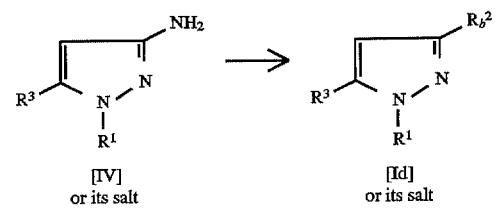

Process 4

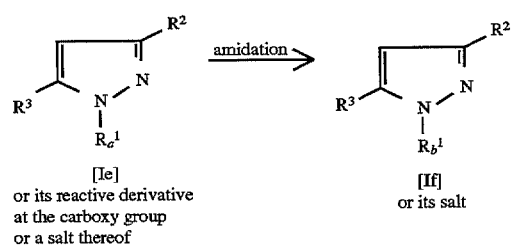

3

-continued

Process 5

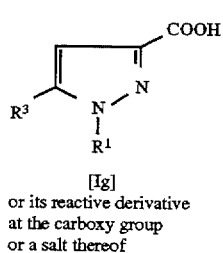 amidation → 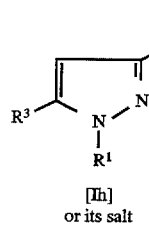

[Ig]
or its reactive derivative
at the carboxy group
or a salt thereof

[Ih]
or its salt

Process 6

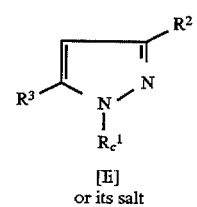 dehydration → 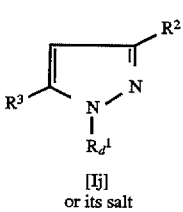

[Ii]
or its salt

[Ij]
or its salt

Process 7

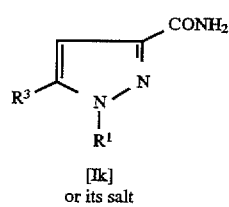 dehydration → 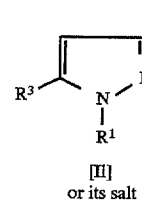

[Ik]
or its salt

[Il]
or its salt

Process 8

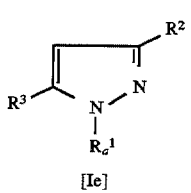 1) CH₂(COOR⁴)₂ [V] 2) hydrolysis → 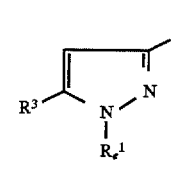

[Ie]
or its reactive derivative
at the carboxy group
or a salt thereof

[Im]

Process 9

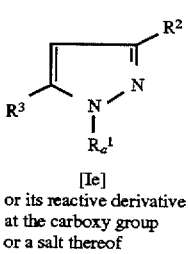 esterification → 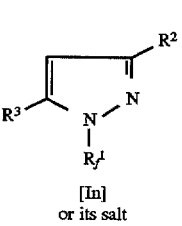

[Ie]
or its reactive derivative
at the carboxy group
or a salt thereof

[In]
or its salt

Process 10

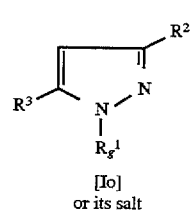 reduction → 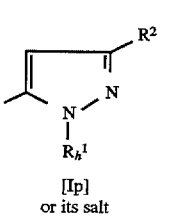

[Io]
or its salt

[Ip]
or its salt

4

-continued

Process 11

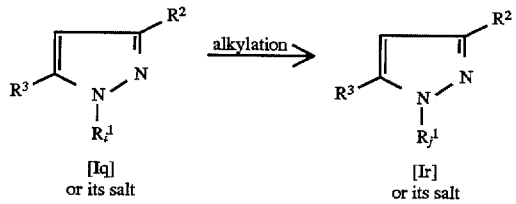 alkylation → 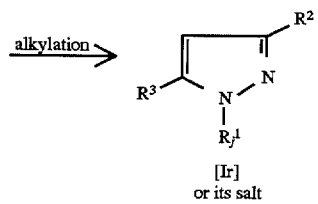

[Iq]
or its salt

[Ir]
or its salt

Process 12

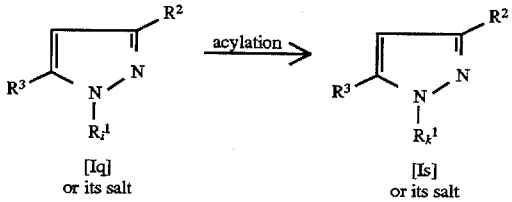 acylation → 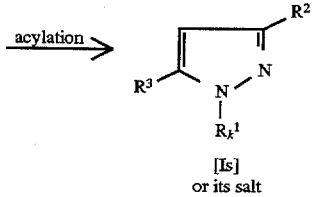

[Iq]
or its salt

[Is]
or its salt

Process 13

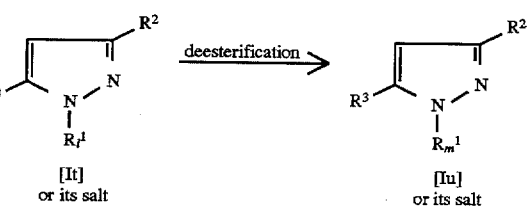 deesterification → 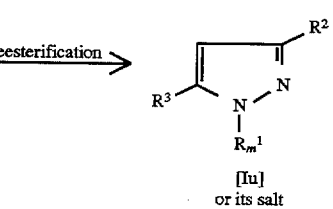

[It]
or its salt

[Iu]
or its salt

Process 14

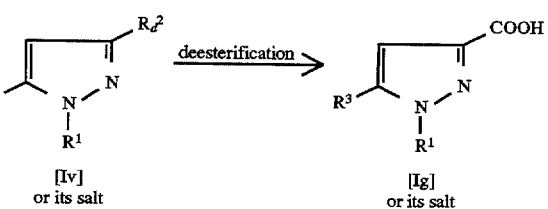 deesterification → 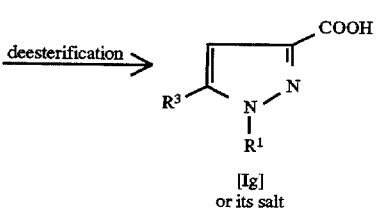

[Iv]
or its salt

[Ig]
or its salt

Process 15

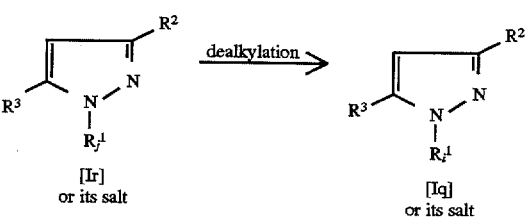 dealkylation → 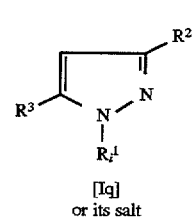

[Ir]
or its salt

[Iq]
or its salt

Process 16

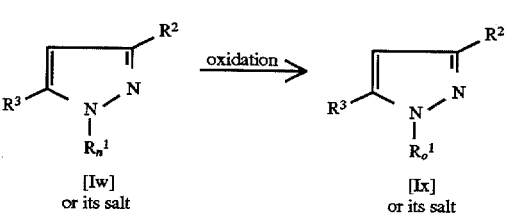 oxidation → 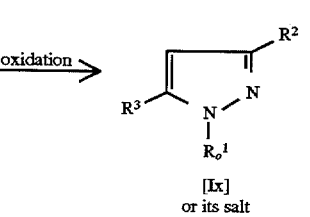

[Iw]
or its salt

[Ix]
or its salt wherein
$R^1$, $R^2$ and $R^3$ are each as defined above,
$R_a{}^2$ is halo(lower)alkyl, cyano or acyl,
$R_a{}^3$ is aryl substituted with lower alkylthio,
$R_b{}^3$ is aryl substituted with lower alkylsulfinyl or lower alkylsulfonyl, $R_b^2$ is halogen, $R_a^1$ is aryl substituted with carboxy, $R_b^1$ is aryl substituted with carbamoyl which may be substituted with substituent selected from the group consisting of lower alkyl, aryl, cyclo(lower)alkyl and hydroxy or N-containing heterocycliccarbonyl, $R_c^2$ is carbamoyl which may be substituted with substituent(s) selected from the group consisting of lower alkyl, aryl, cyclo(lower)alkyl and hydroxy, or N-containing heterocycliccarbonyl, $R_c^1$ is aryl substituted with carbamoyl, $R_d^1$ is aryl substituted with cyano, $R_e^1$ is aryl substituted with acetyl, $R^4$ is lower alkyl, $R_f^1$ is aryl substituted with esterified carboxy, $R_g^1$ is aryl substituted with carboxy or esterified carboxy, $R_h^1$ is aryl substituted with hydroxymethyl, $R_i^1$ aryl substituted with hydroxy, $R_j^1$ is aryl substituted with lower alkoxy optionally substituted with acyl or lower alkoxy, $R_k^1$ is aryl substituted with acyloxy, $R_l^1$ is aryl substituted with lower alkoxy which is substituted with esterified carboxy, $R_m^1$ is aryl substituted with lower alkoxy which is substituted with carboxy, $R_d^2$ is esterified carboxy, $R_n^1$ is aryl substituted with lower alkylthio, and $R_o^1$ is aryl substituted with lower alkylsulfinyl or lower alkylsulfonyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkylthio", "lower alkylsulfonyl", "lower alkylsulfinyl", "hydroxy(lower)alkyl" and "halo(lower)alkyl" may be a straight or branched one such as methyl, ethyl, propyl, isopropyl, butyl, isobutyl, tert-butyl, pentyl, hexyl or the like, in which preferable one is methyl.

Suitable "cyclo(lower)alkyl" may be cyclopropyl, cyclobutyl, cyclopentyl, cyclohexyl and the like, in which preferable one is cyclohexyl.

Suitable "lower alkoxy" may be methoxy, ethoxy, propoxy, isopropoxy, butoxy, isobutoxy, tert-butoxy and the like, in which preferable one is methoxy, ethoxy or isopropoxy.

Suitable "aryl" and aryl moiety in the term "aryloxy" may be phenyl, naphthyl, and the like, in which preferable one is phenyl.

Suitable "halogen" may be fluorine, chlorine, bromine and iodine, in which preferable one is bromine.

Suitable "halo(lower)alkyl" may be chloromethyl, fluoromethyl, bromomethyl, difluoromethyl, dichloromethyl, trifluoromethyl, trichloromethyl, 2-fluoroethyl and the like, in which preferable one is difluoromethyl or trifluoromethyl.

Suitable "lower alkylenedioxy" may be a straight or branched one such as methylenedioxy, ethylenedioxy, trimethylenedioxy, dimethylmethylenedioxy, propylenedioxy or the like.

Suitable "acyl" and acyl moiety in the term "acyloxy" may be carboxy; esterified carboxy; carbamoyl optionally substituted with substituent(s) selected from the group consisting of lower alkyl, cyclo(lower)alkyl, aryl and hydroxy; lower alkanoyl; acryl; lower alkylsulfinyl; lower alkylsulfonyl; N-containing heterocycliccarbonyl; and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like.

The lower alkanoyl may be formyl, acetyl, propionyl, butyryl, isobutyryl, valeryl, isovaleryl, pivaloyl, hexanoyl and the like.

The aroyl may be benzoyl, naphthoyl, benzoyl substituted with lower alkyl [e.g. toluoyl, xyloyl, etc.] and the like.

The N-containing heterocycliccarbonyl may be saturated 5 or 6-membered N-, or N- and S-, or N- and O-containing heterocycliccarbonyl such as pyrrolidinylcarbonyl, imidazolidinylcarbonyl, piperidinocarbonyl, piperazinylcarbonyl, N-(lower)alkylpiperazinylcarbonyl [e.g. N-methylpiperazinylcarbonyl, N-ethylpiperazinylcarbonyl, etc.], morpholinocarbonyl, thiomorpholinocarbonyl or the like.

Suitable "lower alkylthio" may be methylthio, ethylthio, propylthio and the like, in which preferable one is methylthio.

Suitable "lower alkylsulfonyl" may be methylsulfonyl, ethylsulfonyl, propylsulfonyl and the like, in which preferable one is methylsulfonyl.

Suitable "lower alkylsulfinyl" may be methylsulfinyl, ethylsulfinyl, propylsulfinyl and the like, in which preferable one is methylsulfinyl.

Preferable compound [I] is one which has aryl (more preferably phenyl)substituted with cyano, lower alkanoyl or lower alkoxy for $R^1$, halogen or halo(lower)alkyl for $R^2$ and aryl (more preferably phenyl) substituted with lower alkylthio, lower alkylsulfinyl or lower alkylsulfonyl for $R^3$.

More preferable compound [I] is one which has aryl (more preferably phenyl) substituted with methoxy or cyano for $R^1$, bromine, difluoromethyl or trifluoromethyl for $R^2$ and aryl (more preferably phenyl) substituted with methylthio, methylsulfinyl or methylsulfonyl for $R^3$, or aryl (more preferably phenyl) substituted with methoxy for $R^1$, bromine or difluoromethyl for $R^2$ and aryl (more preferably phenyl) substituted with methylthio, methylsulfinyl or methylsulfonyl for $R^3$.

Most preferable compound [I] is one which has 4-methoxyphenyl for $R^1$, bromine or difluoromethyl for $R^2$, or 4-cyanophenyl for $R^1$, trifluoromethyl for $R^2$, and 4-(methylthio)phenyl, 4-(methylsulfinyl)phenyl or 4-(methylsulfonyl)phenyl for $R^3$.

Suitable pharmaceutically acceptable salts of the object compound [I] are conventional non-toxic salts and include a metal salt such as an alkali metal salt [e.g. sodium salt, potassium salt, etc.], an alkaline earth metal salt [e.g. calcium salt, magnesium salt, etc.] or the like.

The processes for preparing the object compound [I] are explained in detail in the following.

Process 1

The compound [Ia] or its salt can be prepared by reacting a compound [II] or its salt with a compound [III] or its salt.

Suitable salts of the compounds [Ia] and [II] may be the same as those exemplified for the compound [I].

Suitable salt of the compound [III] may be the same as those exemplified for the compound [I] and an acid addition salt such as an inorganic acid addition salt [e.g. hydrochloride, hydrobromide, sulfate, phosphate, etc.], an organic acid addition salt [e.g. formate, acetate, trifluoroacetate, methanesulfonate, benzenesulfonate, toluenesulfonate, etc.] or the like.

This reaction is usually carried out in a conventional solvent such as alcohol (e.g. methanol, ethanol, etc.), dioxane, tetrahydrofuran, acetic acid, N,N-dimethylformamide, a mixture thereof or any other organic solvent which does not adversely influence the reaction.

The reaction temperature is not critical, and the reaction is usually carried out under heating.

Process 2

The compound [Ic] or its salt can be prepared by reacting a compound [Ib] or its salt with an oxidizing agent.

Suitable salts of the compounds [Ib] and [Ic] may be the same as those exemplified for the compound [I].

The suitable oxidizing agent may be hydrogen peroxide, cumene hydroperoxide, tert-butyl hydroperoxide, Jones reagent, peracid [e.g. peracetic acid, perbenzoic acid, m-chloroperbenzoic acid, etc.], chromic acid, potassium permanganate, alkali metal periodate [e.g. sodium periodate, etc.] and the like.

This reaction is usually carried out in a solvent which does not adversely influence the reaction such as acetic acid, dichloromethane, acetone, ethyl acetate, chloroform, water, an alcohol [e.g. methanol, ethanol, etc.], a mixture thereof or the like.

The reaction temperature is not critical, and the reaction is usually carried out under cooling to warming.

In this reaction, in case that the compound [Ib] having aryl substituted with lower alkylthio for $R^1$ is used as a starting compound, the compound [Ic] having aryl substituted with lower alkylsulfinyl or lower alkylsulfonyl for $R^1$ may be obtained according to reaction conditions. This case is included within the scope of the present reaction.

Process 3

The compound [Id] or its salt can be prepared by the following methods. Namely, 1) the compound [IV] or its salt is firstly reacted with a nitrite compound, and then 2) the resultant product is reacted with cuprous halide.

Suitable salt of the compound [Id] may be the same as those exemplified for the compound [I].

Suitable salt of the compound [IV] may be the same as those exemplified for the compound [III]in Process 1.

Suitable nitrite compound may be alkali metal nitrite [e.g. sodium nitrite, potassium nitrite, etc.], alkyl nitrite [e.g. tert-butyl nitrite, etc.] and the like.

Suitable cuprous halide may be cuprous chloride, cuprous bromide and the like.

In the first step, the reaction is preferably carried out in the presence of an acid [e.g. sulfuric acid, etc.].

The reaction is usually carried out in a solvent such as water, tetrahydrofuran, dioxane, acetonitrile or any other organic solvent which does not adversely influence the reaction, or a mixture thereof.

The reaction temperature is not critical and the reaction can be carried out under cooling to warming.

In the second step, the reaction is preferably carried out in the presence of alkali metal halide [e.g. sodium bromide, etc.] and an inorganic acid [e.g. hydrobromic acid, etc.].

The reaction is usually carried out in a solvent such as water, tetrahydrofuran, dioxane or any other organic solvent which does not adversely influence the reaction.

The reaction temperature is not critical and the reaction can be carried out warming to heating.

Process 4

The compound [If] or its salt can be prepared by reacting a compound [Ie] or its reactive derivative at the carboxy group or a salt thereof with an amine, or formamide and alkali metal alkoxide.

Suitable salts of the compounds [If] and [Ie] and its reactive derivative at the carboxy group may be the same as those exemplified for the compound [I].

Suitable "amine" may be ammonia, lower alkylamine, arylamine, cyclo(lower)alkylamine, lower alkylhydroxylamine, N-containing heterocyclic compound and the like.

The lower alkylamine may be mono or di(lower)alkylamine such as methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine or the like.

The arylamine may be aniline, naphthylamine and the like. The cyclo(lower)alkylamine may be cyclopropylamine, cyclobutylamine, cyclopentylamine, cyclohexylamine and the like.

The lower alkylhydroxylamine may be methylhydroxylamine, ethylhydroxylamine, propylhydroxylamine, butylhydroxylamine, isopropylhydroxylamine and the like.

The N-containing heterocyclic compound may be saturated 5 or 6-membered N-, or N- and S-, or N- and O-containing heterocyclic compound such as pyrrolidine, imidazolidine, piperidine, piperazine, N-(lower)alkylpiperazine [e.g. N-methylpiperazine, N-ethylpiperazine, etc.], morpholine, thiomorpholine or the like.

Suitable "alkali metal alkoxide" may be sodium methoxide, sodium ethoxide, potassium tert-butoxide and the like.

Suitable reactive derivative at the carboxy group of the compound [Ie] may include an ester, an acid halide, an acid anhydride and the like. The suitable examples of the reactive derivatives may be an acid halide [e.g. acid chloride, acid bromide, etc.];

a symmetrical acid anhydride;

a mixed acid anhydride with 1,1'-carbonyl diimidazole or an acid such as aliphatic acid [e.g. acetic acid, pivalic acid, etc.], substituted phosphoric acid [e.g. dialkylphosphoric acid, diphenylphosphoric acid, etc.];

an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, formamide, ethyl acetate, N,N-dimethylformamide, pyridine or any other organic solvent which does not adversely influence the reaction. Among these solvents, hydrophilic solvents may be used in a mixture with water.

When the compound [Ie] is used in a free acid form in the reaction, the reaction is preferably carried out in the presence of a conventional condensing agent such as N,N'-dicyclohexylcarbodiimide, N-cyclohexyl-N'- morpholinoethylcarbodiimide, N-ethyl-N'-(3-dimethylamino-propyl)carbodiimide, thionyl chloride, oxalyl chloride, lower alkoxycarbonyl halide [e.g. ethyl chloroformate, isobutyl chloroformate, etc.], 1-(p-chlorobenzene-sulfonyloxy)-6-chloro-1H-benzotriazole, or the like. The reaction is also preferably carried out in the presence of a conventional base such as triethylamine, pyridine, sodium hydroxide or the like.

The reaction temperature is not critical, and the reaction can be carried out under cooling to heating.

Process 5

The compound [Ih] or its salt can be prepared by reacting a compound [Ig] or its reactive derivative at the carboxy group or a salt thereof with an amine, or formamide and alkali metal alkoxide.

Suitable salts of the compounds [Ih] and [Ig] and its reactive derivative at the carboxy group may be the same as those exemplified for the compound [I].

This reaction can be carried out in substantially the same manner as that of Process 4, and therefore the reaction mode and reaction conditions [e.g. solvent, reaction temperature, etc.] of this reaction are to be referred to those explained in Process 4.

Process 6

The compound [Ij] or its salt can be prepared by reacting a compound [Ii] or its salt with a dehydrating agent.

Suitable salts of the compounds [Ii] and [Ij] may be the same as those exemplified for the compound [I].

Suitable dehydrating agent may be phosphorus compound [e.g. phosphorus pentoxide, phosphorus pentachloride, phosphorus oxychloride, etc.], thionyl chloride, acid anhydride [e.g. acetic anhydride, etc.], phosgene, arylsulphonyl chloride [e.g. benzenesulfonyl chloride, p-toluenesulfonyl chloride, etc.], methanesulfonyl chloride, sulfamic acid, ammonium sulfamate, N,N'-dicyclohexylcarbodiimide, lower alkoxycarbonyl halide [e.g. ethyl chloroformate, etc.] and the like.

The reaction is usually carried out in a conventional solvent such as acetonitrile, methylene chloride, ethylene chloride, benzene, N,N-dimethylformamide, pyridine or any other organic solvent which does not adversely influence the reaction.

Additionally in case that the above-mentioned dehydrating agents are in liquid, they can also be used as a solvent.

The reaction temperature is not critical and the reaction is preferably carried out under warming or heating.

Process 7

The compound [Il] or its salt can be prepared by reacting a compound [Ik] or its salt with a dehydrating agent.

Suitable salts of the compounds [Ik] and [Il] may be the same as those exemplified for the compound [I].

This reaction can be carried out in substantially the same manner as that of Process 6, and therefore the reaction mode and reaction conditions [e.g. solvent, reaction temperature, etc.] of the reaction are to be referred to those explained in Process 6.

Process 8

The compound [Im] can be prepared by the following methods.

Namely, 1) the compound [Ie] or its reactive derivative at the carboxy group or a salt thereof is firstly reacted with a compound [V], and then 2) subjecting the resultant product to hydrolysis reaction.

Suitable salts of the compound [Ie] and its reactive derivative at the carboxy group may be the same as those exemplified for the compound [I].

Suitable reactive derivative at the carboxy group of the compound [Ie] may be an acid halide [e.g. acid chloride, acid bromide, etc.], and the like.

In the first step, the reaction is preferably carried out in the presence of a base such as an alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] and the like.

The reaction is usually carried out in a solvent which does not adversely influence the reaction such as diethyl ether, tetrahydrofuran, dioxane and the like.

The reaction temperature is not critical and the reaction can be carried out under cooling to heating.

In this reaction, a compound of the formula:

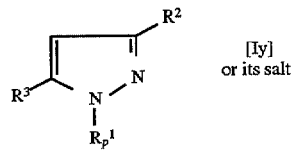

[Iy] or its salt wherein

R² and R³ are each as defined above, and $R_p^1$ is aryl substituted with di(lower alkoxycarbonyl) acetyl, may be obtained.

Suitable salt of the compound [Iy] may be the same as those exemplified for the compound [I].

The compound [Iy] or its salt is further subjected to hydrolysis to give the compound [Im].

The hydrolysis is preferably carried out in the presence of an acid.

Suitable acid may be an organic acid [e.g. formic acid, acetic acid, propionic acid, trifluoroacetic acid, trichloroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to heating.

Process 9

The compound [In] or its salt can be prepared by reacting a compound [Ie] or its reactive derivative at the carboxy group or a salt thereof with a hydroxy compound.

Suitable salts of the compounds [In] and [Ie] and its reactive derivative at the carboxy group may be the same as those exemplified for the compound [I].

Suitable reactive derivative at the carboxy group of the compound [Ie] may be acid halide [e.g. acid chloride, acid bromide, etc.] and the like.

Suitable hydroxy compound may be an alcohol [e.g. methanol, ethanol, propanol, benzyl alcohol, etc.], phenol, naphthol and the like.

The reaction is usually carried out in a conventional solvent such as diethyl ether, tetrahydrofuran, dioxane or any other organic solvent which does not adversely influence the reaction.

Additionally, in case that the above-mentioned hydroxy compound is in liquid, it can also be used as a solvent.

The reaction temperature is not critical and the reaction is usually carried out under cooling to heating.

When the compound [Ie] is used in a free acid form in the reaction, the reaction is preferably carried out in the presence of an acid.

Suitable acid may be an inorganic acid exemplified in the above-mentioned Process 8.

Process 10

The compound [Ip] or its salt can be prepared by reacting a compound [Io] or its salt with a reducing agent.

Suitable salts of the compound [Io] and [Ip] may be the same as those exemplified for the compound [I].

Suitable reducing agent may be diborane, lithium aluminum hydride and the like.

The reaction is usually carried out in a conventional solvent such as diethyl ether, tetrahydrofuran or any other organic solvent which does not adversely influence the reaction.

The reaction temperature is not critical, and the reaction can be carried out under cooling to heating.

Process 11

The compound [Ir] or its salt can be prepared by reacting a compound [Iq] or its salt with an alkylating agent.

Suitable salts of the compounds [Iq] and [Ir] may be the same as those exemplified for the compound [I].

Suitable alkylating agent may be lower alkyl halide, in which alkyl may be substituted with lower alkoxy or acyl [e.g. methyl iodide, ethyl bromide, chloromethyl methyl ether, ethyl bromoacetate, etc.].

The reaction is preferably carried out in the presence of a base such as an alkali metal [e.g. sodium, potassium, etc.], an alkaline earth metal [e.g. magnesium, calcium, etc.], the hydride or hydroxide or carbonate or bicarbonate thereof.

The reaction is usually carried out in a conventional solvent which does not adversely influence the reaction such as water, dioxane, an alcohol [e.g. methanol, ethanol, etc.], acetonitrile, tetrahydrofuran, N,N-dimethylformamide, or a mixture thereof. Additionally, in case that the above-mentioned alkylating agents are in liquid, they can also be used as a solvent.

The reaction temperature is not critical and the reaction can be carried out under cooling to heating.

In this reaction, in case that the compound [Iq] having aryl substituted with hydroxy for $R^3$ is used as a starting compound, the compound [Ir] having aryl substituted with lower alkoxy for $R^3$ may be obtained according to reaction conditions. This case is included within the scope of the present reaction.

Process 12

The compound [Is] or its salt can be prepared by reacting a compound [Iq] or its salt with an acylating agent.

Suitable salts of the compounds [Iq] and [Is] may be the same as those exemplified for the compound [I].

The acylating agent may include an organic acid represented by the formula: $R^5$—OH, in which $R^5$ is acyl as illustrated above, or its reactive derivative.

The suitable reactive derivative of organic acid may be a conventional one such as an acid halide [e.g. acid chloride, acid bromide, etc.], an acid azide, an acid anhydride, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction temperature is not critical, and the reaction can be carried out under cooling to heating.

Process 13

The compound [Iu] or its salt can be prepared by subjecting a compound [It] or its salt to deesterification reaction.

Suitable salts of the compounds [It] and [Iu] may be the same as those exemplified for the compound [I].

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diaza-bicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 14

The compound [Ig] or its salt can be prepared by subjecting a compound [Iv] or its salt to deesterification reaction.

Suitable salts of the compounds [Ig] and [Iv] may be the same as those exemplified for the compound [I].

This reaction can be carried out in substantially the same manner as that of Process 13, and therefore the reaction mode and reaction conditions [e.g. solvent, reaction temperature, etc.] of this reaction are to be referred to those explained in Process 13.

Process 15

The compound [Iq] or its salt can be prepared by subjecting a compound [Ir] or its salt to dealkylation reaction.

Suitable salts of the compounds [Iq] and [Ir] may be the same as those exemplified for the compound [I].

The reaction is carried out in accordance with a conventional method such as hydrolysis or the like.

The hydrolysis is preferably carried out in the presence of an acid including Lewis acid [e.g. hydrochloric acid, hydrobromic acid, hydroiodic acid, boron tribromide, boron trichloride, etc.] or tri(lower alkyl)silyliodide [e.g. trimethylsilyliodide, etc.].

The reaction is usually carried out in a solvent such as water, acetic acid, methylene chloride, tetrahydrofuran, a mixture thereof or any other solvent which does not adversely influence the reaction.

The reaction temperature is not critical and the reaction is usually carried out under cooling to heating.

In this reaction, in case that the compound [Ir] having aryl substituted with lower alkoxy for $R^3$ is used as a starting compound, the compound [Iq] having aryl substituted with hydroxy for $R^3$ may be obtained according to reaction conditions. This case is included within the scope of the present reaction.

Process 16

The compound [Ix] or its salt can be prepared by reacting a compound [Iw] or its salt with an oxidizing agent.

Suitable salts of the compounds [Iw] and [Ix] may be the same as those exemplified for the compound [I].

This reaction can be carried out in substantially the same manner as that of Process 2, and therefore the reaction mode and reaction conditions [e.g. solvent, reaction temperature, etc.] of this reaction are to be referred to those explained in Process 2.

In this reaction, in case that the compound [Iw] having aryl substituted with lower alkylthio for $R^3$ is used as a starting compound, the compound [Ix] having aryl substituted with lower alkylsulfinyl or lower alkylsulfonyl for $R^3$ may be obtained according to reaction conditions. This case is included within the scope of the present reaction.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compound [I] or its pharmaceutically acceptable salts thereof possesses strong antiinflammatory, analgesic and antithrombotic activities, and are useful for the treatment and/or prevention of inflammatory conditions, various pains, collagen diseases, autoimmune diseases, various immunity diseases and thrombosis in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atropic gastritis, gastritis varialoforme, ulcerative colitis, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lupus erythematosus, scleroderma, polymyositis, periarteritis nodosa, rheumatic fever, Sjögren's syndrome, Behcet disease, thyroiditis, type I diabetes, nephrotic syndrome, aplastic anemia, myasthenia gravis, uveitis, contact dermatitis, psoriasis, Kawasaki disease, sarcoidosis, Hodgkin's disease and the like. Additionally, the object compound is expected to be useful as therapeutical and/or preventive agents for cardiovascular or cerebrovascular diseases, the diseases caused by hyperglycemia and hyperlipemia.

In order to illustrate the usefulness of the object compound [I], the pharmacological test data of the compound [I] are shown in the following.

[A] ANTIINFLAMMATORY ACTIVITY;

Effect on adjuvant arthritis in rats:

(i) Test Method:

Ten female Sprague-Dawley rats were used per group. A dose of 0.5 mg of *Mycobacterium tuberculosis* (strain Aoyama B) suspended in 0.05 ml of liquid paraffin was injected subcutaneously in the right hind paw. The injection of mycobacterial adjuvant produced local inflammatory lesions (primary lesion) and then about 10 days later, secondary lesions in both the injected and uninjected paws. The difference in volumes of both paws before and after adjuvant injection was the measure of arthritis. The drug was given orally once a day for 23 consecutive days from day 1.

(ii) Test Results:

| Test compound (Example No.) | Dose (mg/kg) | Inhibition of secondary lesion (uninjected paw) (%) |
| --- | --- | --- |
| 1 | 3.2 | 93.6 |
| 2 | 3.2 | 89.3 |
| 3 | 3.2 | 99.1 |
| 4 | 3.2 | 81.0 |
| 7 | 3.2 | 100 |
| 8-6) | 3.2 | 95.7 |
| 13-4) | 3.2 | 95.6 |
| 28-1) | 3.2 | 100 |
| 28-2) | 3.2 | 100 |
| Ibuprofen | 100 | 79.6 |

[B] ANALGESIC ACTIVITY:

Inflammatory hyperalgesia induced by brewer's yeast in rats:

(i) Test Method:

Ten male Sprague Dawley rats were used per group. 0.1 ml of 5% brewer's yeast suspended in 0.5% methylcellulose was injected into the right hind paw. The pain threshold was determined 3 hours after yeast injection, by applying pressure to the foot and reading the pressure at which the rat withdrew the foot.

The drugs were given orally 2 hours after yeast injection. The pain threshold in the treated animals was compared with that in the control animals.

(ii) Test Results:

| Test compound (Example No.) | Dose (mg/kg) | Relative potency (Control = 1.0) |
| --- | --- | --- |
| 1 | 10 | 1.36 |
| 2 | 10 | 1.38 |
| 3 | 10 | 1.47 |
| 9 | 10 | 1.53 |

[C] ANTI-RHEUMATIC ACTIVITY:
Effect on collagen induced arthritis in mice:
(i) Test Method:

Eight male DBA/1 mice were used per group. Type II bovine collagen was solublized in 0.1M acetic acid and emulsified in complete Freund's adjuvant (CFA). Mice were primed with 0.2 mg of Type II collagen in CFA intradermally at the base of the tail. Mice were challenged after 21 day with the same procedure. From 10 day after challenge, drug was administered orally once a day for 3 weeks and mice were inspected weekly for visual signs of arthritis. An arthritis index was used to grade limb 0–3, representing joint swelling and erythema (Grade 1), visible joint disorder (Grade 2) and detectable joint ankylosis (Grade 3).

(ii) Test Results:

| Test compound (Example No.) | Dose (mg/kg) | Inhibition of arthritis index (%) |
| --- | --- | --- |
| 1 | 10 | 51.3 |
| 2 | 10 | 61.7 |
| 7 | 10 | 83.3 |

For therapeutic purpose, the compound [I] and a pharmaceutically acceptable salt thereof of the present invention can be used in a form of pharmaceutical preparation containing one of said compounds as an active ingredient, in admixture with a pharmaceutically acceptable carrier such as an organic or inorganic solid or liquid excipient suitable for oral, parenteral or external (topical) administration. The pharmaceutical preparations may be capsules, tablets, dragees, granules, inhalant, suppositories, solution, lotion, suspension, emulsion, ointment, gel, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

PREPARATION 1

A mixture of ethyl 1-(4-methoxyphenyl)-5-[4-(methylthio)phenyl]pyrazole-3-carboxylate (10.2 g) and potassium hydroxide (3.7 g) in methanol (60 ml) was refluxed for 30 minutes. The solvent was evaporated, and the residue was dissolved in water and washed with toluene. The aqueous layer was acidified, and the precipitates were collected and washed with ethyl acetate to give crystals of 1-(4-methoxyphenyl)-5-[4-(methylthio)phenyl]pyrazole-3-carboxylic acid (8.8 g).

mp: 238°–239° C. (dec.)

IR (Nujol): 2750, 2600, 1700, 1600, 1510 cm$^{-1}$

Mass (m/z): 340 (M$^+$).

PREPARATION 2

A mixture of 1-(4-methoxyphenyl)-5-[4-(methylthio)phenyl]pyrazole-3-carboxylic acid (3.4 g) and phosphorus pentachloride (2.3 g) in dichloromethane (20 ml) was stirred at ambient temperature for 1 hour. The solvent was evaporated to give an oil of the corresponding acid chloride.

A solution of the obtained oil in acetone (10 ml) was added dropwise to an ice-cooled mixture of sodium azide (0.65 g), water (10 ml) and acetone (10 ml). During the addition of the above solution, the reaction mixture was kept at pH 8 to 9 by addition of an aqueous sodium bicarbonate solution. The mixture was stirred at ambient temperature for 30 minutes, concentrated in vacuo, and extracted with ethyl acetate. The extract was washed with water, dried, and concentrated to give an oil of the corresponding acid azide.

The above oil was dissolved in toluene (50 ml). The solution was heated at 100° C. for 1 hour and concentrated to give a solid of the corresponding isocyanate.

A mixture of the above solid and concentrated hydrochloric acid (10 ml) in acetic acid (10 ml) was refluxed for 5 hours, and then concentrated. A solution of sodium hydroxide was added to the residue and the mixture was extracted with chloroform. The extract was washed with water, dried, and concentrated in vacuo. The residue was purified by column chromatography on silica gel eluting with chloroform and the purified product was recrystallized from ethanol to give crystals of 1-(4-methoxyphenyl)-5-[4-(methylthio)phenyl]pyrazol-3-amine (0.8 g).

mp: 120°–129° C.

IR (Nujol): 3450, 3300, 3200, 1630, 1610, 1565, 1520 cm$^{-1}$

NMR (CDCl$_3$, δ): 2.46 (3H, s), 3.32 (2H, broad s), 3.80 (3H, s), 5.87 (1H, s), 6.7–7.2 (8H, m)

Mass (m/z): 311 (M$^+$)

EXAMPLE 1

A mixture of 4,4-difluoro-1-[4-(methylthio)phenyl]-butane-1,3-dione (2.4 g) and 4-methoxyphenylhydrazine hydrochloride (1.9 g) in acetic acid (10 ml) was stirred at 100° C. for 1 hour. The solvent was evaporated and the residue was purified by column chromatography on silica gel (30 g) eluting with toluene. The purified oily product was crystallized from ethanol to give crystals of 3-(difluoromethyl)-1-(4-methoxyphenyl)-5-[4-(methylthio)phenyl]pyrazole (2.5 g).

mp: 100°–101° C.

IR (Nujol): 1610, 1520, 1500 cm$^{-1}$

NMR (CDCl$_3$, δ): 2.48 (3H, s), 3.82 (3H, s), 6.5–7.3 (10H, m)

Mass (m/z): 346 (M$^+$)

EXAMPLE 2

A mixture of 3-(difluoromethyl)-1-(4-methoxyphenyl)-5-[4-(methylthio)phenyl]pyrazole (1 g) and m-chloroperbenzoic acid (0.56 g) in dichloromethane (23 ml) was stirred at ambient temperature for 1 hour. The mixture was washed with an aqueous solution of sodium bicarbonate, dried over magnesium sulfate, and concentrated. The oily residue was crystallized from ethanol to give crystals of 3-(difluoromethyl)-1-(4-methoxyphenyl)-5-[4-(methylsulfinyl)phenyl]pyrazole (0.82 g).

mp: 123°–124° C.

IR (Nujol): 1615, 1590, 1520 cm$^{-1}$

NMR (CDCl$_3$, δ): 2.74 (3H, s), 3.83 (3H, s), 6.5–7.7 (10H, m)

EXAMPLE 3

A mixture of 3-(difluoromethyl)-1-(4-methoxyphenyl)-5-[4-(methylthio)phenyl]pyrazole (2 g), 30% hydrogen peroxide (2 ml) and sulfuric acid (2 drops) in acetic acid (5 ml) was stirred at 60° C. for 1 hour. The solvent was evaporated and the residue was recrystallized from ethyl acetate to give crystals of 3-(difluoromethyl)-1-(4-methoxyphenyl)-5-[4-(methylsulfonyl)phenyl]pyrazole (0.86 g).

mp: 135° C.

IR (Nujol): 1605, 1520 cm$^{-1}$

NMR (CDCl$_3$, δ): 3.07 (3H, s), 3.84 (3H, s), 6.1–8.0 (10H, m)

Mass (m/z): 378 (M$^+$), 346

EXAMPLE 4

A solution of sodium nitrite (492 mg) in water (0.6 ml) was added dropwise to a mixture of 1-(4-methoxyphenyl)-5-[4-(methylthio)phenyl]pyrazol-3-amine (2 g) and sulfuric acid (1.2 ml) in water (3 ml) and acetonitrile (6 ml) at 5° C., and the mixture was stirred at the same temperature for 1 hour. The mixture was added portionwise to a mixture of cuprous bromide (1.25 g), sodium bromide (1.2 g) and hydrobromic acid (3.3 ml) in water (6 ml) at 70° to 80° C. during a period of 15 minutes, and the resulting mixture was stirred at 80° C. for 30 minutes. The aqueous layer was removed by decantation and the oily residue was extracted with toluene. The extract was washed with water, dried, and concentrated in vacuo. The residue (1.1 g) was purified by column chromatography on silica gel (20 g) eluting with a mixture of chloroform and n-hexane (2:1) to give crystals of 3-bromo-1-(4-methoxyphenyl)-5-[4-(methylthio)phenyl]pyrazole (0.62 g).

mp: 144°–145° C.

IR (Nujol): 1605, 1510 cm$^{-1}$

NMR (CDCl$_3$, δ): 2.47 (3H, s), 3.81 (3H, s), 6.47 (1H, s), 6.8–7.3 (8H, m)

Mass (m/z): 376 (M$^+$)

EXAMPLE 5

A mixture of 1-[4-(methylthio)phenyl]-4,4,4-trifluorobutane-1,3-dione (1.8 g) and 4-cyanophenylhydrazine hydrochloride (1.2 g) in acetic acid (30 ml) and N,N-dimethylformamide (1 ml) was stirred at 110° C. for 3 hours. The reaction mixture was poured into water and extracted with ethyl acetate. The extract was washed with water, dried over anhydrous magnesium sulfate, and evaporated to give a brown powder of 1-(4-cyanophenyl)-5-[4-(methylthio)phenyl]-3-(trifluoromethyl)pyrazole (2.5 g).

mp: 145°–147° C.

IR (Nujol): 2230, 1610, 1595, 1515 cm$^{-1}$

NMR (CDCl$_3$, δ): 2.50 (3H, s), 6.75 (1H, s), 7.0–7.8 (8H, m)

Mass (m/z): 359 (M$^+$)

EXAMPLE 6

The following compounds were obtained according to a similar manner to that of Example 5.

1) 3-(Difluoromethyl)-1-[3,4-(methylenedioxy)phenyl]-5-[4-(methylthio)phenyl]pyrazole IR (Film): 1605, 1520, 1485 cm$^{-1}$ NMR (CDCl$_3$, δ): 2.48 (3H, s), 5.99 (2H, s), 6.6–7.3 (9H, m)

Mass (m/z): 360 (M$^+$)

2) 1-(4-Carboxyphenyl)-3-(difluoromethyl)-5-[4-(methylthio)phenyl]pyrazole mp: 195°–200° C. (dec.)

IR (Nujol): 2650, 2520, 1700, 1640, 1610, 1515 cm$^{-1}$

NMR (DMSO-d$_6$, δ): 2.47 (3H, s), 6.9–8.1 (10H, m)

Mass (m/z): 360 (M$^+$)

3) 1-(4-Carboxyphenyl)-5-[4-(methylthio)phenyl]-3-(trifluoromethyl)pyrazole mp: 148°–151° C.

IR (Nujol): 2650, 1700, 1610, 1500 cm$^{-1}$

NMR (DMSO-d$_6$, δ): 2.51 (3H, s), 7.2–8.2 (9H, m), 13.2 (1H, s)

Mass (m/z): 378 (M$^+$)

4) 5-[4-(Methylthio)phenyl]-1-[4-phenoxyphenyl]-3-(trifluoromethyl)pyrazole

IR (Film): 1590 cm$^{-1}$

NMR (CDCl$_3$, δ): 2.48 (3H, s), 6.72 (1H, s), 6.9–7.5 (13H, m)

Mass (m/z): 426 (M$^+$)

5) 1-[3,4-(Methylenedioxy)phenyl]-5-[4-(methylthio)phenyl]-3-(trifluoromethyl)pyrazole IR (Film): 1590, 1490 cm$^{-1}$ NMR (CDCl$_3$, δ): 2.48 (3H, s), 6.02 (2H, s), 6.6–7.3 (8H, m)

Mass (m/z): 378 (M$^+$)

6) Ethyl 1-(4-carboxyphenyl)-5-[4-(methylthio)phenyl]pyrazole-3-carboxylate mp: 145°–146° C.

IR (Nujol): 1720, 1695, 1610, 1515 cm$^{-1}$

NMR (CDCl$_3$, δ): 1.43 (3H, t, J=7 Hz), 2.49 (3H, s), 4.47 (2H, q, J=7 Hz), 7.03 (1H, s), 7.1–7.3 (4H, m), 7.47 (2H, d, J=8 Hz), 8.10 (2H, d, J=8 Hz)

Mass (m/z): 382 (M$^+$)

7) Ethyl 1-[3,4-(methylenedioxy)phenyl]-5-[4-(methylthio)phenyl]pyrazole-3-carboxylate NMR (CDCl$_3$, δ): 1.42 (3H, t, J=7 Hz), 2.48 (3H, s), 4.44 (2H, q, J=7 Hz), 6.02 (2H, s), 6.7–7.4 (8H, m)

Mass (m/z): 382 (M$^+$)

EXAMPLE 7

A mixture of 1-(4-cyanophenyl)-5-[4-(methylthio)phenyl]-3-(trifluoromethyl)pyrazole (2.5 g) and m-chloroperbenzoic acid (3.2 g) in dichloromethane (100 ml) was stirred at ambient temperature for 2 hours. The mixture was washed with an aqueous solution of sodium bicarbonate, dried, and concentrated. The oily residue (3 g) was purified by column chromatography on silica gel eluting with a mixture of chloroform and methanol (40:1). The purified product (2.1 g) was recrystallized from a mixture of isopropanol and ethanol to give yellow crystals of 1-(4-cyanophenyl)-5-[4-(methylsulfonyl)phenyl]-3-(trifluoromethyl)pyrazole (1.3 g).

mp: 140°–142° C.

IR (Nujol): 2230, 1610, 1515, 1500 cm$^{-1}$

NMR (CDCl$_3$, δ): 3.11 (3H, s), 6.89 (1H, s), 7.4–8.0 (8H, m)

Mass (m/z): 391 (M$^+$)

EXAMPLE 8

The following compounds were obtained according to a similar manner to that of Example 7.

1) 3-(Difluoromethyl)-1-[3,4-(methylenedioxy)phenyl]-5-[4-(methylsulfonyl)phenyl]pyrazole mp: 120°–121° C.

IR (Nujol): 1600, 1505, 1490 cm$^{-1}$

NMR (CDCl$_3$, δ): 3.08 (3H, s), 6.05 (2H, s), 6.5–7.1 (5H, m), 7.45 (2H, d, J=8 Hz), 7.91 (2H, d, J=8 Hz)

Mass (m/z): 392 (M$^+$)

2) 1-(4-Carbamoylphenyl)-3-(difluoromethyl)-5-[4-(methylsulfonyl)phenyl]pyrazole mp: 245°–246° C.

IR (Nujol): 3430, 3370, 3250, 1650, 1615, 1575, 1520 cm$^{-1}$

NMR (DMSO-d$_6$, δ): 3.26 (3H, s), 7.1–8.1 (12H, m)

Mass (m/z): 391 (M$^+$), 375

3) 1-(4-Cyanophenyl)-3-(difluoromethyl)-5-[4-methylsulfonyl)phenyl]pyrazole mp: 140°–141° C.

IR (Nujol): 2230, 1610, 1515 cm$^{-1}$

NMR (CDCl$_3$, δ): 3.11 (3H, s), 6.5–7.5 (6H, m), 7.70 (2H, d, J=8 Hz), 7.96 (2H, d, J=8 Hz)

Mass (m/z): 373 (M$^+$)

4) 1-(4-Acetylphenyl)-3-(difluoromethyl)-5-[4-(methylsulfonyl)phenyl]pyrazole mp: 121°–122° C.

IR (Nujol): 1685, 1600, 1515 cm$^{-1}$

NMR (CDCl$_3$, δ): 2.63 (3H, s), 3.10 (3H, s), 6.5–7.5 (6H, m), 7.9–8.1 (4H, m)

Mass (m/z): 390 (M$^+$), 375

5) 5-[4-(Methylsulfonyl)phenyl]-1-(4-phenoxyphenyl)-3-(trifluoromethyl)pyrazole mp: 132°–133° C.

IR (Nujol): 1590, 1515, 1500 cm$^{-1}$

NMR (CDCl$_3$, δ): 3.08 (3H, s), 6.85 (1H, s), 6.9–8.0 (13H, m)

Mass (m/z): 458 (M$^+$)

6) 1-(4-Acetylphenyl)-5-[4-(methylsulfonyl)phenyl]-3-(trifluoromethyl)pyrazole mp: 120°–122° C.

IR (Nujol): 1690, 1605, 1500 cm$^{-1}$

NMR (CDCl$_3$, δ): 2.63 (3H, s), 3.10 (3H, s), 6.64 (1H, s), 7.1–8.0 (8H, m)

Mass (m/z): 408 (M$^+$)

7) 1-[3,4-(Methylenedioxy)phenyl]-5-[4-(methylsulfonyl)phenyl]-3-(trifluoromethyl)pyrazole mp: 110°–111° C.

IR (Nujol): 1605, 1510 cm$^{-1}$

NMR (CDCl$_3$, δ): 3.09 (3H, s), 6.06 (2H, s), 6.6–6.9 (4H, m), 7.45 (2H, d, J=8 Hz), 7.92 (2H, d, J=8 Hz)

Mass (m/z): 410 (M$^+$)

8) N-Methyl-1-(4-cyanophenyl)-5-[4-(methylsulfonyl)phenyl]pyrazole-3-carboxamide mp: 228°–230° C.

NMR (CDCl$_3$, δ): 3.04 (3H, d, J=5 Hz), 3.10 (3H, s), 6.9–8.0 (10H, m)

Mass (m/z): 380 (M$^+$)

9) Ethyl 1-(4-acetylphenyl)-5-[4-(methylsulfonyl)phenyl]pyrazole-3-carboxylate

IR (Nujol): 1720, 1685, 1605, 1510 cm$^{-1}$

NMR (CDCl$_3$, δ): 1.44 (3H, t, J=7 Hz), 2.63 (3H, s), 3.09 (3H, s), 4.48 (2H, q, J=7 Hz), 7.15 (1H, s), 7.3–7.5 (4H, m), 7.8–8.0 (4H, m)

Mass (m/z): 412 (M$^+$)

10) Ethyl 1-[3,4-(methylenedioxy)phenyl]-5-[4-methylsulfonyl)phenyl]pyrazole-3-carboxylate mp: 188°–190° C. (dec.)

IR (Nujol): 1715, 1605, 1505 cm$^{-1}$

NMR (CDCl$_3$, δ): 1.43 (3H, t, J=7 Hz), 3.08 (3H, s), 4.46 (2H, q, J=7 Hz), 6.05 (2H, s), 6.7–8.0 (8H, m)

Mass (m/z): 414 (M$^+$)

11) 1-(4-Methoxyphenyl)-5-[4-(methylsulfonyl)phenyl]-3-(trifluoromethyl)pyrazole mp: 155°–156° C.

IR (Nujol): 1600, 1500 cm$^{-1}$

NMR (DMSO$_6$, δ): 3.25 (3H, s), 3.80 (3H, s), 7.03 (2H, d, J=8 Hz), 7.2–7.6 (5H, m), 7.93 (2H, d, J=8 Hz)

Mass (m/z): 396 (M$^+$)

12) 3-(Chloromethyl)-1-(4-methoxyphenyl)-5-[4-(methylsulfonyl)phenyl]pyrazole mp: 115°–116° C.

IR (Nujol): 1600, 1510 cm$^{-1}$

NMR (CDCl$_3$, δ): 3.07 (3H, s), 3.83 (3H, s), 4.70 (2H, s), 6.68 (1H, s), 6.8–7.9 (8H, m)

Mass (m/z): 376 (M$^+$)

13) 3-(Difluoromethyl)-1-(2-methoxyphenyl)-5-[4-(methylsulfonyl)phenyl]pyrazole mp: 152°–153° C.

IR (Nujol): 1600, 1510, 1500 cm$^{-1}$

NMR (CDCl$_3$, δ): 3.04 (3H, s), 3.46 (3H, s), 6.5–7.5 (8H, m), 7.85 (2H, d, J=8 Hz)

Mass (m/z): 378 (M$^+$)

14) 1-(4-Methoxyphenyl)-5-[2-(methylsulfonyl)phenyl]-3-(trifluoromethyl)pyrazole mp: 128°–129° C.

IR (Nujol): 1615, 1590, 1520, 1495 cm$^{-1}$

NMR (CDCl$_3$, δ): 2.87 (3H, s), 3.75 (3H, s), 6.7–6.9 (3H, m), 7.2–8.2 (6H, m)

Mass (m/z): 396 (M$^+$)

15) 3-(Difluoromethyl)-1-(4-methoxyphenyl)-5-[2-(methylsulfonyl)phenyl]pyrazole mp: 124°–125° C.

IR (Nujol): 1615, 1595, 1520, 1495 cm$^{-1}$

NMR (CDCl$_3$, δ): 2.90 (3H, s), 3.75 (3H, s), 6.5–7.4 (7H, m), 7.5–8.2 (3H, m)

Mass (m/z): 378 (M$^+$)

16) 1-Cyclohexyl-5-[4-(methylsulfonyl)phenyl]-3-(trifluoromethyl)pyrazole mp: 180°–181° C.

IR (Nujol): 1610, 1505 cm$^{-1}$

NMR (CDCl$_3$, δ): 1.1–2.2 (10H, m), 3.14 (3H, s), 3.9–4.2 (1H, m), 6.55 (1H, s), 7.57 (2H, d, J=8 Hz), 8.08 (2H, d, J=8 Hz)

Mass (m/z): 372 (M$^+$), 291

EXAMPLE 9

A mixture of 3-(difluoromethyl)-1-[3,4-(methylenedioxy)phenyl]-5-[4-(methylthio)phenyl]pyrazole (2.7 g) and m-chloroperbenzoic acid (1.8 g) in dichloromethane (80 ml) was stirred at 5° C. for 4 hours. The mixture was washed with an aqueous solution of sodium bicarbonate, dried, and concentrated. The residue (2.9 g) was purified by column chromatography on silica gel eluting with a mixture of chloroform and methanol (25:1). The purified product (1.3 g) was recrystallized from isopropanol to give 3-(difluoromethyl)-1-[3,4-(methylenedioxy)phenyl]-5-[4-(methylsulfinyl)phenyl]pyrazole (0.85 g).

mp: 104°–105° C.

IR (Nujol): 1610, 1510, 1490 cm$^{-1}$

NMR (DMSO$_6$, δ): 2.77 (3H, s), 6.12 (2H, s), 6.7–7.8 (9H, m)

Mass (m/z): 376 (M$^+$), 359

EXAMPLE 10

A suspension of 1-(4-carboxyphenyl)-3-(difluoromethyl)-5-[4-(methylthio)phenyl]pyrazole (3.6 g) in thionyl chloride (40 ml) was refluxed for 4 hours, and then concentrated in vacuo. A solution of the residue in tetrahydrofuran (30 ml) was added to a stirred mixture of ammonium hydroxide (28%, 50 ml) and tetrahydrofuran (50 ml) at 5° C., and the resulting mixture was stirred at the same temperature for 1.5 hours. The mixture was acidified with hydrochloric acid and extracted with ethyl acetate. The extract was washed with water, dried, and evaporated to give 1-(4-carbamoylphenyl)-3-(difluoromethyl)-5-[4-(methylthio)phenyl]pyrazole (3.6 g).

mp: 198°–201° C. (dec.)

IR (Nujol): 3450, 3360, 1650, 1610, 1575 cm$^{-1}$

NMR (DMSO$_6$, δ): 2.47 (3H, s), 6.8–8.1 (12H, m)

Mass (m/z): 359 (M$^+$)

EXAMPLE 11

The following compounds were obtained according to a similar manner to that of Example 10.

1) Ethyl 1-(4-carbamoylphenyl)-5-[4-(methylthio)phenyl]pyrazole-3-carboxylate mp: 172°–174° C.

IR (Nujol): 3450, 3200, 1715, 1660, 1615 cm$^{-1}$

NMR (CDCl$_3$, δ): 1.43 (3H, t, J=7 Hz), 2.48 (3H, s), 4.46 (2H, q, J=7 Hz), 6.0 (2H, broad peak), 7.0–7.9 (9H, m)

Mass (m/z): 381 (M$^+$)

2) 1-(4-Carbamoylphenyl)-5-[4-(methylsulfonyl)phenyl]-3-(trifluoromethyl)pyrazole mp: 210°–215° C. (dec.)

IR (Nujol): 3430, 3300, 3190, 1660, 1620, 1580 cm$^{-1}$

NMR (DMSO$_6$, δ): 3.26 (3H, s), 7.3–8.2 (11H, m)

Mass (m/z): 409 (M$^+$), 393

3) N-Methyl-1-(4-cyanophenyl)-5-[4-(methylthio)phenyl]pyrazole-3-carboxamide mp: 210°–220° C. (dec.)

NMR (CDCl$_3$, δ): 2.50 (3H, s), 3.02 (3H, d, J=4 Hz), 6.9–7.7 (9H, m)

Mass (m/z): 348 (M$^+$)

4) 1-(4-Carbamoylphenyl)-5-[4-(methylsulfonyl)phenyl]pyrazole-3-carbonitrile mp: 222°–224° C.

IR (Nujol): 3470, 3350, 2250, 1660, 1610, 1510 cm$^{-1}$

NMR (DMSO$_6$, δ): 3.26 (3H, s), 7.4–7.6 (6H, m), 7.9–8.2 (5H, m)

Mass (m/z): 366 (M$^+$), 350

EXAMPLE 12

A solution of phosphorus oxychloride (1.7 g) in N,N-dimethylformamide (20 ml) was stirred at 5° C. for 30 minutes. To the solution was added 1-(4-carbamoylphenyl)-3-(difluoromethyl)-5-[4-(methylsulfonyl)phenyl]pyrazole (2 g). The resulting mixture was stirred at 5° C. for 2 hours, poured into ice-water, and extracted with a mixture of tetrahydrofuran and ethyl acetate. The extract was washed with water, dried, and evaporated to give an oil of 1-(4-cyanophenyl)-3-(difluoromethyl)-5-[4-(methylthio)phenyl]pyrazole (2.0 g).

IR (Nujol): 2240, 1610, 1515, 1500 cm$^{-1}$

NMR (CDCl$_3$, δ): 2.50 (3H, s), 6.5–7.7 (10H, m)

Mass (m/z): 341 (M$^+$)

EXAMPLE 13

The following compounds were obtained according to a similar manner to that of Example 12.

1) Ethyl 1-(4-cyanophenyl)-5-[4-(methylthio)phenyl]pyrazole-3-carboxylate mp: 143°–145° C. (dec.)

IR (Nujol): 2250, 1725, 1605, 1510 cm$^{-1}$

NMR (CDCl$_3$, δ): 1.43 (3H, t, J=7 Hz), 2.50 (3H, s), 4.46 (2H, q, J=7 Hz), 7.0–7.7 (9H, m)

Mass (m/z): 363 (M$^+$)

2) 1-(4-Carboxyphenyl)-5-[4-(methylsulfonyl)phenyl]pyrazole-3-carbonitrile mp: 185°–190° C. (dec.)

IR (Nujol): 2250, 1720, 1610, 1515 cm$^{-1}$

NMR (DMSO$_6$, δ): 3.26 (3H, s), 7.4–8.1 (9H, m)

Mass (m/z): 367 (M$^+$)

3) 1-(4-Cyanophenyl)-5-[4-(methylsulfonyl)phenyl]pyrazole-3-carbonitrile mp: 159°–160° C.

IR (Nujol): 2250, 2240, 1610, 1550, 1505 cm$^{-1}$

NMR (CDCl$_3$, δ): 3.11 (3H, s), 7.01 (1H, s), 7.4–8.0 (8H, m)

Mass (m/z): 348 (M$^+$)

4) 1-(4-Acetylphenyl)-5-[4-(methylsulfonyl)phenyl] pyrazole-3-carbonitrile mp: 155°–156° C.

IR (Nujol): 2250, 1695, 1605, 1510 cm$^{-1}$

NMR (CDCl$_3$, δ): 2.64 (3H, s), 3.10 (3H, s), 6.99 (1H, s), 7.1–8.1 (8H, m)

Mass (m/z): 365 (M$^+$), 350

5) 1-[3,4-(Methylenedioxy)phenyl]-5-[4-(methylsulfonyl)phenyl]pyrazole-3-carbonitrile mp: 182°–183° C.

IR (Nujol): 2250, 1605, 1495 cm$^{-1}$

NMR (CDCl$_3$, δ): 3.09 (3H, s), 6.07 (2H, s), 6.6–6.9 (3H, m), 6.94 (1H, s), 7.43 (2H, d, J=8 Hz), 7.93 (2H, d, J=8 Hz)

Mass (m/z): 367 (M$^+$)

EXAMPLE 14

A mixture of 1-(4-carboxyphenyl)-3-(difluoromethyl)-5-[4-(methylthio)phenyl]pyrazole (2 g) and thionyl chloride (20 ml) was refluxed for 3 hours, and concentrated in vacuo, giving 1-[4-(chloroformyl)phenyl]-3-(difluoromethyl)-5-[4-(methylthio)phenyl]pyrazole. A solution of diethyl malonate (1.4 g) and ethanol (0.3 ml) in diethyl ether (15 ml) was added dropwise to a stirred mixture of magnesium (0.16 g), ethanol (0.2 ml) and carbon tetrachloride (0.36 ml) in diethyl ether (5 ml). The resulting mixture was refluxed for 1 hour. A solution of the above acid chloride in tetrahydrofuran (15 ml) was added dropwise to the mixture. The mixture was stirred at ambient temperature for 1 hour and refluxed for 1 hour. The reaction mixture was poured into diluted hydrochloric acid and extracted with ethyl acetate. The extract was washed with water, dried, and concentrated. A mixture of the residue (4 g), acetic acid (40 ml), and 20% sulfuric acid (20 ml) was refluxed for 3.5 hours and then concentrated. The residue was dissolved in ethyl acetate, and the solution was washed with water, dried, and concentrated. The residue was purified by column chromatography on silica gel eluting with a mixture of toluene and ethyl acetate (4:1) to give crystals of 1-(4-acetylphenyl)-3-(difluoromethyl)-5-[4-(methylthio)phenyl]pyrazole (0.4 g).

mp: 143°–145° C.

IR (Nujol): 1680, 1600 cm$^{-1}$

NMR (CDCl$_3$, δ): 2.49 (3H, s), 2.61 (3H, s), 6.5–7.5 (8H, m), 7.95 (2H, d, J=7 Hz)

Mass (m/z): 358 (M$^+$)

EXAMPLE 15

The following compounds were obtained according to a similar manner to that of Example 14.

1) 1-(4-Acetylphenyl)-5-[4-(methylthio)phenyl]-3-(trifluoromethyl)pyrazole

IR (Film): 1690, 1610, 1500 cm$^{-1}$

NMR (CDCl$_3$, δ): 2.49 (3H, s), 2.61 (3H, s), 6.75 (1H, s), 7.1–8.2 (8H, m)

Mass (m/z): 376 (M$^+$)

2) Ethyl 1-(4-acetylphenyl)-5-[4-(methylthio) phenyl]pyrazole-3-carboxylate

IR (Film): 1725, 1690, 1600, 1515 cm$^{-1}$

NMR (CDCl$_3$, δ): 1.43 (3H, t, J=7 Hz), 2.49 (3H, s), 2.62 (3H, s), 4.46 (2H, q, J=7 Hz), 7.02 (1H, s), 7.1–7.2 (4H, m), 7.46 (2H, d, J=8 Hz), 7.95 (2H, d, J=8 Hz)

Mass (m/z): 380 (M$^+$)

EXAMPLE 16

A mixture of 1-(4-carboxyphenyl)-5-[4-(methylthio)phenyl]-3-(trifluoromethyl)pyrazole (3.55 g) and 30% hydrogen peroxide (5.5 ml) in acetic acid (25 ml) was stirred at 45° C. for 2 hours. The mixture was poured into ice-water, and the precipitates were collected, washed with water, and recrystallized from ethanol to give 1-(4-carboxyphenyl)-5-[4-(methylsulfonyl)phenyl]-3-(trifluoromethyl)pyrazole (3.2 g).

mp: 250°–252° C. (dec.)

IR (Nujol): 3450, 2650, 1700, 1615, 1500 cm$^{-1}$

NMR (DMSO$_6$, δ): 3.26 (3H, s), 7.4–8.3 (9H, m)

Mass (m/z): 410 (M$^+$)

EXAMPLE 17

The following compound was obtained according to a similar manner to that of Example 16.

Ethyl 1-(4-carboxyphenyl)-5-[4-(methylsulfonyl) phenyl]pyrazole-3-carboxylate mp: 267°–268° C.

IR (Nujol): 1720, 1610, 1515 cm$^{-1}$

NMR (DMSO$_6$, δ): 1.33 (3H, t, J=7 Hz), 3.26 (3H, s), 4.36 (2H, q, J=7 Hz), 7.34 (1H, s), 7.4–7.6 (4H, m), 7.9–8.1 (4H, m), 13.2 (1H, s)

Mass (m/z): 414 (M$^+$)

EXAMPLE 18

A mixture of 1-(4-carboxyphenyl)-5-[4-(methylsulfonyl)phenyl]-3-(trifluoromethyl)pyrazole (2.2 g) and hydrogen chloride in ethanol (50 ml) was refluxed for 6 hours. The solvent was evaporated and the residue was recrystallized from ethanol to give crystals of 1-[4-(ethoxycarbonyl)phenyl]-5-[4-(methylsulfonyl)phenyl]-3-(trifluoromethyl)pyrazole (2.3 g).

mp: 159°–161° C.

IR (Nujol): 1730, 1610, 1510 cm$^{-1}$

NMR (DMSO$_6$, δ): 1.36 (3H, t, J=7 Hz), 3.27 (3H, s), 4.38 (2H, q, J=7 Hz), 7.5–8.3 (9H, m)

Mass (m/z): 438 (M$^+$), 406

EXAMPLE 19

A mixture of 1-[4-(ethoxycarbonyl)phenyl]-5-[4-(methylsulfonyl)phenyl]-3-(trifluoromethyl)pyrazole (2.4 g) and lithium aluminum hydride (0.25 g) in tetrahydrofuran (20 ml) was stirred at 55° C. for 2 hours. The reaction was quenched with methanol and water, and the mixture was filtered. The filtrate was concentrated and the residue was dissolved in a mixture of ethyl acetate and tetrahydrofuran. The solution was washed with water, dried, and evaporated. The residue was purified by column chromatography on silica gel eluting with a mixture of chloroform and methanol (20:1) to give a white powder of 1-[4-(hydroxymethyl) phenyl]-5-[4-(methylsulfonyl)phenyl]-3-(trifluoromethyl) pyrazole (1.3 g).

mp: 129°–133° C.

IR (Nujol): 3450, 1610, 1520, 1500 cm$^{-1}$

NMR (CDCl$_3$, δ): 3.09 (3H, s), 4.7–4.9 (2H, m), 6.8–8.1 (9H, m)

Mass (m/z): 396 (M$^+$), 364

EXAMPLE 20

Sodium hydride (0.17 g) was added to a solution of 1-(4-hydroxyphenyl)-5-[4-(methylsulfonyl)phenyl]-3-(trifluoromethyl)pyrazole (1.5 g) in N,N-dimethylformamide (15 ml) at 5° C. The mixture was stirred at ambient temperature for 30 minutes. To the mixture was added chloromethyl methyl ether (0.4 g) in N,N-dimethylformamide (2 ml) at 5° C. The obtained mixture was stirred at 5° C. for 2 hours and at ambient temperature for 1 hour, poured into a mixture of ice and dilute hydrochloric acid, and extracted with ethyl acetate. The extract was washed with water, dried, and evaporated. The residue (1.3 g) was recrystallized from isopropanol to give crystals of 1-[4-(methoxymethoxy)phenyl]-5-[4-(methylsulfonyl) phenyl]-3-(trifluoromethyl)pyrazole (1.3 g).

mp: 96°–97° C.

IR (Nujol): 1610, 1520, 1500 cm$^{-1}$

NMR (CDCl$_3$, δ): 3.08 (3H, s), 3.49 (3H, s), 5.20 (2H, s), 6.84 (1H, s), 7.0–8.0 (8H, m)

Mass (m/z): 426 (M$^+$)

EXAMPLE 21

The following compounds were obtained according to a similar manner to that of Example 20.

1) Ethyl 4-{5-[4-(methylsulfonyl)phenyl]-3-(trifluoromethyl)-1-pyrazolyl}phenoxyacetate.

mp: 87°–89° C.

IR (Nujol): 1755, 1610, 1520, 1500 cm$^{-1}$

NMR (CDCl$_3$, δ): 1.30 (3H, t, J=7 Hz), 3.08 (3H, s), 4.28 (2H, t, J=7 Hz), 4.65 (2H, s), 6.84 (1H, s), 6.8–8.0 (8H, m)

Mass (m/z): 468 (M$^+$)

2) 3-(Difluoromethyl)-1-[4-(methoxymethoxy) phenyl]-5-[4-(methylsulfonyl)phenyl]pyrazole mp: 95°–96° C.

IR (Nujol): 1610, 1520 cm$^{-1}$

NMR (CDCl$_3$, δ): 3.08 (3H, s), 3.49 (3H, s), 5.19 (2H, s), 6.5–7.5 (8H, m), 7.92 (2H, d, J=8 Hz)

Mass (m/z): 408

3) 1-(4-Ethoxyphenyl)-5-[4-(methylsulfonyl)phenyl]-3-(trifluoromethyl)pyrazole mp: 140° C.

IR (Nujol): 1610, 1600, 1520, 1500 cm$^{-1}$

NMR (CDCl$_3$, δ): 1.43 (3H, t, J=7 Hz), 3.07 (3H, s), 4.05 (2H, q, J=7 Hz), 6.8–7.5 (7H, m), 7.91 (2H, d, J=8 Hz)

Mass (m/z): 410 (M$^+$)

4) 1-(4-Isopropoxyphenyl)-5-[4-(methylsulfonyl) phenyl]-3-(trifluoromethyl)pyrazole mp: 99°–100° C.

IR (Nujol): 1610, 1525, 1510 cm$^{-1}$

NMR (CDCl$_3$, δ): 1.35 (6H, d, J=6 Hz), 3.07 (3H, s), 4.4–4.7 (1H, m), 6.8–7.5 (7H, m), 7.90 (2H, d, J=8 Hz)

Mass (m/z): 424 (M$^+$)

5) 3-(Difluoromethyl)-1-(4-ethoxyphenyl)-5-[4-(methylsulfonyl)phenyl]pyrazole mp: 105°–107° C.

IR (Nujol): 1605, 1520, 1500 cm$^{-1}$

NMR (CDCl$_3$, δ): 1.43 (3H, t, J=7 Hz), 3.07 (3H, s), 4.05 (2H, q, J=7 Hz), 6.5–7.5 (8H, m), 7.89 (2H, d, J=8 Hz)

Mass (m/z): 392 (M$^+$)

6) 3-(Difluoromethyl)-1-(4-isopropoxyphenyl)-5-[4-(methylsulfonyl)phenyl]pyrazole mp: 90° C.

IR (Nujol): 1605, 1515, 1500 cm$^{-1}$

NMR (CDCl$_3$, δ): 1.35 (6H, d, J=6 Hz), 3.07 (3H, s), 4.4–4.7 (1H, m), 6.5–7.5 (8H, m), 7.89 (2H, d, J=8 Hz)

Mass (m/z): 406 (M$^+$)

EXAMPLE 22

Acetyl chloride (0.31 g) was added dropwise to an ice-cooled solution of 1-(4-hydroxyphenyl)-5-[4-(methylsulfonyl)phenyl]-3-(trifluoromethyl)pyrazole (1 g) in pyridine (10 ml). The mixture was stirred at 5° C. for 3 hours, poured into water, and acidified with hydrochloric acid. The precipitates were filtered and purified by column chromatography on silica gel eluting with a mixture of chloroform and methanol (20:1) to give a yellow powder of 1-(4-acetoxyphenyl)-5-[4-(methylsulfonyl)phenyl]-3-(trifluoromethyl)pyrazole (0.9 g).

mp: 142°–145° C.

IR (Nujol): 1760, 1605, 1500 cm$^{-1}$

NMR (CDCl$_3$, δ): 2.32 (3H, s), 3.08 (3H, s), 6.85 (1H, s), 7.1–7.5 (6H, m), 7.93 (2H, d, J=8 Hz)

Mass (m/z): 424 (M$^+$), 382

EXAMPLE 23

A mixture of ethyl 4-{5-[4-(methylsulfonyl)phenyl]-3-(trifluoromethyl)-1-pyrazolyl}phenoxyacetate (1.7 g), 10% sodium hydroxide (10 ml) in tetrahydrofuran (10 ml) and ethanol (40 ml) was refluxed for 3 hours. The solvent was evaporated, and the residue was dissolved in water and acidified with hydrochloric acid. The precipitates were filtered and recrystallized from a mixture of tetrahydrofuran, ethanol, and isopropyl ether to give 4-{5-[4-(methylsulfonyl)phenyl]-3-(trifluoromethyl)-1-pyrazolyl}phenoxyacetic acid (1.1 g).

mp: 245°–250° C. (dec.)

IR (Nujol): 1720, 1610, 1520, 1500 cm$^{-1}$

NMR (DMSO$_6$, δ): 3.25 (3H, s), 4.43 (2H, s), 6.9–8.0 (9H, m)

Mass (m/z): 440 (M$^+$)

EXAMPLE 24

A mixture of ethyl 1-(4-cyanophenyl)-5-[4-(methylthio) phenyl]pyrazole-3-carboxylate (2.8 g) and 1N sodium hydroxide (10 ml) in ethanol (150 ml) and tetrahydrofuran (20 ml) was stirred at ambient temperature for 3 hours. The solvent was evaporated, and the residue was dissolved in water, acidified with hydrochloric acid, and extracted with ethyl acetate. The extract was washed with water, dried, and evaporated to give 1-(4-cyanophenyl)-5-[4-(methylthio) phenyl]pyrazole-3-carboxylic acid (2.5 g).

mp: 168°–173° C. (dec.)

IR (Nujol): 2240, 1710, 1605, 1510 cm$^{-1}$

NMR (CDCL$_3$, δ): 2.50 (3H, s), 7.0–7.7 (9H, m)

Mass (m/z): 335 (M$^+$)

EXAMPLE 25

A mixture of ethyl 1-(4-carboxyphenyl)-5-[4-(methylsulfonyl)phenyl]pyrazole-3-carboxylate (3.9 g) and sodium methoxide (3 g) in formamide (40 ml) was stirred at 45° C. for 3 hours. The mixture was poured into a mixture of ice-water and hydrochloric acid. The precipitates were collected, washed with water, and dried to give crystals of 1-(4-carboxyphenyl)-5-[4-(methylsulfonyl)phenyl]pyrazole-3-carboxamide (3.2 g).

mp: 292°–293° C.

IR (Nujol): 3430, 3350, 3200, 1715, 1695, 1650, 1590 cm$^{-1}$

NMR (DMSO$_6$, δ): 3.26 (3H, s), 7.19 (1H, s), 7.4–8.1 (10H, m), 13.2 (1H, s)

Mass (m/z): 385 (M$^+$)

EXAMPLE 26

The following compounds were obtained according to a similar manner to that of Example 25.

1) 1-(4-Acetylphenyl)-5-[4-(methylsulfonyl)phenyl]pyrazole-3-carboxamide mp: 242°–245° C. (dec.)

IR (Nujol): 3480, 3200, 1685, 1605 cm$^{-1}$

NMR (DMSO$_6$, δ): 2.61 (3H, s), 3.26 (3H, s), 7.18 (1H, s), 7.4–8.1 (10H, m)

Mass (m/z): 383 (M$^+$), 368

2) 1-[3,4-Methylenedioxy)phenyl]-5-[4-(methylsulfonyl)phenyl]pyrazole-3-carboxamide mp: 283°–285° C.

IR (Nujol): 3500, 3300, 1670, 1585, 1510 cm$^{-1}$

NMR (DMSO$_6$, δ): 3.25 (3H, s), 6.13 (2H, s), 6.7–8.0 (10H, m)

Mass (m/z): 385 (M$^+$)

EXAMPLE 27

The following compounds were obtained according to a similar manner to that of Example 1.

1) 1-(4-Methoxyphenyl)-5-[4-(methylthio)phenyl]-3-trifluoromethyl)pyrazole mp: 98°–100° C.

IR (Nujol): 1605, 1520, 1500 cm$^{-1}$

NMR (CDCl$_3$, δ): 2.48 (3H, s), 3.82 (3H, s), 6.71 (1H, s), 6.8–7.3 (8H, m)

Mass (m/z): 364 (M$^+$)

2) 3-(Chloromethyl)-1-(4-methoxyphenyl-1)-5-[4-(methylthio)phenyl]pyrazole

IR (Film): 1600, 1510 cm$^{-1}$

NMR (CDCl$_3$, δ): 2.47 (3H, s), 3.82 (3H, s), 4.70 (2H, s), 6.5–7.7 (9H, m)

Mass (m/z): 344 (M$^+$)

3) 3-(Difluoromethyl)-1-(2-methoxyphenyl)-5-[4-(methylthio)phenyl]pyrazole mp: 98°–100° C.

IR (Nujol): 1605, 1515, 1500 cm$^{-1}$

NMR (CDCl$_3$, δ): 2.44 (3H, s), 3.50 (3H, s), 6.4–7.5 (10H, m)

Mass (m/z): 346 (M$^+$)

4) 1-(4-Methoxyphenyl)-5-[2-(methylthio)phenyl]-3-(trifluoromethyl)pyrazole mp: 78°–80° C.

IR (Nujol): 1610, 1590, 1520, 1490 cm$^{-1}$

NMR (CDCl$_3$, δ): 2.34 (3H, s), 3.77 (3H, s), 6.6–7.4 (9H, m)

Mass (m/z): 364 (M$^+$)

5) 3-(Difluoromethyl)-1-(4-methoxyphenyl)-5-[2-(methylthio)phenyl]pyrazole mp: 79°–81° C.

IR (Nujol): 1615, 1590, 1520, 1490 cm$^{-1}$

NMR (CDCl$_3$, δ): 2.33 (3H, s), 3.76 (3H, s), 6.5–7.4 (10H, m)

Mass (m/z): 346 (M$^+$)

6) 3-(Difluoromethyl)-5-(4-methoxyphenyl)-1-[4-(methylthio)phenyl]pyrazole mp: 90°–92° C.

IR (Nujol): 1610, 1545, 1495 cm$^{-1}$

NMR (CDCl$_3$, δ): 2.49 (3H, s), 3.81 (3H, s), 6.4–7.3 (10H, m)

Mass (m/z): 347 ((M+1)$^+$)

7) 1-Cyclohexyl-5-[4-(methylthio)phenyl]-3-(trifluoromethyl)pyrazole

IR (Nujol): 1605, 1595, 1545 cm$^{-1}$

NMR (CDCl$_3$, δ): 1.1–2.1 (10H, m), 2.53 (3H, s), 4.0–4.2 (1H, m), 6.45 (1H, s), 7.2–7.4 (4H, m)

Mass (m/z): 340 (M$^+$)

8) 1-[4-(Methylthio)phenyl]-5-(4-nitrophenyl)-3-(trifluoromethyl)pyrazole mp: 156°–157° C.

IR (Nujol): 1600, 1520, 1490 cm$^{-1}$

NMR (CDCl$_3$, δ): 2.50 (3H, s), 6.87 (1H, s), 7.1–7.5 (6H, m), 8.15–8.3 (2H, m)

Mass (m/z): 380 ((M+1)$^+$)

EXAMPLE 28

The following compounds were obtained according to a similar manner to that of Example 2.

1) 3-Bromo-1-(4-methoxyphenyl)-5-[4-(methylsulfinyl)phenyl]pyrazole mp: 140°–142° C.

IR (Nujol): 1610, 1585, 1515 cm$^{-1}$

NMR (DMSO-d$_6$, δ): 2.75 (3H, s), 3.83 (3H, s), 6.60 (1H, s), 6.85–7.63 (8H, m)

Mass (m/z): 392, 390, 377

2) 1-(4-Cyanophenyl)-5-[4-(methylsulfinyl)phenyl]-3-(trifluoromethyl)pyrazole mp: 121°–122° C.

IR (Nujol): 1605, 1510, 1495 cm$^{-1}$

NMR (CDCl$_3$, δ): 2.78 (3H, s), 6.85 (1H, s), 7.3–7.8 (8H, m)

Mass (m/z): 375 (M$^+$)

3) 1-(4-Acetylphenyl)-5-[4-(methylsulfinyl)phenyl]-3-(trifluoromethyl)pyrazole mp: 145°–146° C.

IR (Nujol): 1690, 1600, 1500 cm$^{-1}$

NMR (CDCl$_3$, δ): 2.62 (3H, s), 2.76 (3H, s), 6.84 (1H, s), 7.3–8.0 (8H, m)

Mass (m/z): 393 ((M+1)⁺)

4) 3-(Difluoromethyl)-5-(4-methoxyphenyl)-1-[4-(methylsulfinyl)phenyl]pyrazole mp: 123°–124° C.

IR (Nujol): 1610, 1550, 1500 cm⁻¹

NMR (CDCl₃, δ): 2.74 (3H, s), 3.83 (3H, s), 6.4–7.7 (10H, m)

Mass (m/z): 363 ((M+1)⁺)

EXAMPLE 29

The following compounds were obtained according to a similar manner to that of Example 3.

1) 3-Bromo-1-(4-methoxyphenyl)-5-[4-(methylsulfonyl)phenyl]pyrazole mp: 177°–178° C.

IR (Nujol): 1610, 1515 cm⁻¹

NMR (DMSO₆, δ): 3.13 (3H, s), 3.79 (3H, s), 6.97–7.93 (9H, m)

Mass (m/z): 408, 406

2) 3-(Difluoromethyl)-5-(4-methoxyphenyl)-1-[4-(methylsulfonyl)phenyl]pyrazole mp: 118°–120° C.

IR (Nujol): 1615, 1595, 1500 cm⁻¹

NMR (CDCl₃, δ): 3.07 (3H, s), 3.84 (3H, s), 6.4–8.0 (10H, m)

Mass (m/z): 379 ((M+1)⁺)

3) 1-[4-(Methylsulfonyl)phenyl]-5-(4-nitrophenyl)-3-(trifluoromethyl)pyrazole mp: 201°–203° C.

IR (Nujol): 1595, 1515 cm⁻¹

NMR (CDCl₃, δ): 3.09 (3H, s), 6.92 (1H, s), 7.4–7.6 (4H, m), 7.9–8.3 (4H, m)

Mass (m/z): 412 ((M+1)⁺)

EXAMPLE 30

Boron tribromide (1M in dichloromethane; 11 ml) was added to an ice-cooled solution of 1-(4-methoxyphenyl)-5-(methylsulfonyl)phenyl]-3-(trifluoromethyl)pyrazole (1.4 g) in dichloromethane (30 ml). The mixture was stirred at 5° C. for 2 hours and concentrated in vacuo. The residue was triturated in dilute hydrochloric acid. The obtained powder was recrystallized from ethanol to give colorless crystals of 1-(4-hydroxyphenyl)-5-[4-(methylsulfonyl)phenyl]-3-(trifluoromethyl)pyrazole (0.91 g).

mp: 243°–244° C.

IR (Nujol): 3370, 1605, 1525, 1505 cm⁻¹

NMR (DMSO₆, δ): 3.25 (3H, s), 6.83 (2H, d, J=8 Hz), 7.1–7.6 (5H, m), 7.92 (2H, d, J=8 Hz), 10.0 (1H, s)

Mass (m/z): 382 (M⁺)

EXAMPLE 31

The following compound was obtained according to a similar manner to that of Example 30.

1-(4-Hydroxyphenyl)-5-[4-(methylsulfonyl)phenyl]-3-(difluoromethyl)pyrazole mp: 170°–180° C.

IR (Nujol): 1595, 1500 cm⁻¹

NMR (DMSO₆, δ): 3.25 (3H, s), 6.7–7.6 (8H, m), 7.92 (2H, d, J=8 Hz), 9.29 (1H, s)

Mass (m/z): 364 (M⁺)

EXAMPLE 32

To a solution of L-(+)-diethyl tartrate (3.71 g) in dichloromethane (75 ml) was added titanium (IV) isopropoxide (2.7 ml) under the atmosphere of nitrogen. After being stirred for 5 minutes, water (162 μl) was added to the mixture. After the mixture was vigorously stirred for 25 minutes, 3-(difluoromethyl)-1-(4-methoxyphenyl)-5-[4-(methylthio)phenyl]pyrazole (6.24 g) was added to the mixture and the solution was cooled to −30° C. and stirred for 40 minutes at −30° C. to −20° C. To the mixture was added dropwise cumene hydroperoxide (3.00 ml). After an additional 10 minutes, the reaction mixture was sealed and allowed to stand overnight at −23° C. Water (3.03 ml) was added to the mixture and the mixture was stirred at ambient temperature for 90 minutes. The reaction mixture was filtered and to the filtrate were added 2N sodium hydroxide (48 ml) and brine (24 ml). After being stirred for 1 hour at ambient temperature, the organic layer was separated, dried over magnesium sulfate and concentrated in vacuo. The residue was purified by column chromatography on silica gel (450 g) eluting with a mixture of dichloromethane and methanol (40:1). The obtained product was recrystallized eight times from a mixture of ethanol and isopropyl ether (1:4) to give R-(+)-3-(difluoromethyl)-1-(4-methoxyphenyl)-5-[4-(metylsulfinyl)phenyl]pyrazole (0.71 g).

mp: 113°–114° C.

[α]_D^{20}=+69.4° (c=1.00 CHCl₃)

IR (Nujol): 1615, 1590, 1520 cm⁻¹

NMR (CDCl₃δ): 2.74 (3H, s), 3.83 (3H, s), 6.5–7.7 (10H, m)

Mass (m/z): 363 ((M+1)⁺)

EXAMPLE 33

The following compound was obtained according to a similar manner to that of Example 32, except that D-(−)-diethyl tartrate was used.

S-(−)-3-(Difluoromethyl)-1-(4-methoxyphenyl)-5-[4-(methylsulfinyl)phenyl]pyrazole mp: 112°–114° C.

[α]_D^{20}=−70.9° (c=1.02, CHCl₃)

IR (Nujol): 1610, 1590, 1515 cm⁻¹

NMR (CDCl₃, δ): 2.75 (3H, s), 3.83 (3H, s), 6.5–7.7 (10H, m)

Mass (m/z): 363 ((M+1)⁺)

What we claim is:

1. A compound of the formula:

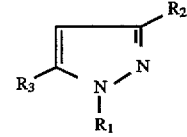 (I)

wherein

R¹ is aryl which is substituted with substituent(s) selected from the group consisting of hydroxy(lower)alkyl, lower alkylenedioxy, carboxy, esterified carboxy, carbamoyl, lower alkanoyloxy, aryloxy and lower alkoxy substituted with acyl or lower alkoxy, $R^2$ is halogen, halo(lower)alkyl, cyano or acyl, and
$R^3$ is aryl substituted with lower alkylthio, lower alkylsulfinyl or lower alkylsulfonyl;
$R^1$ is phenyl substituted with methoxy,
$R^2$ is difluoromethyl and
$R^3$ is phenyl substituted with methylsulfinyl; or
$R^1$ is phenyl which is substituted with lower alkylthio, lower alkylsulfinyl or lower alkylsulfonyl,
$R^2$ is difluoromethyl and
$R^3$ is phenyl substituted with methoxy.

2. A compound of the formula:

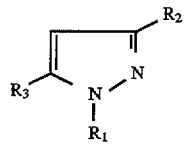 (I)

wherein $R^1$ is phenyl substituted with methoxy,
$R^2$ is difluoromethyl and
$R^3$ is phenyl substituted with methylsulfinyl.

3. The compound of claim 1, which is 3-(difluoromethyl)-1-(4-methoxyphenyl)-5-[4-methylsulfinyl)phenyl]pyrazole.

4. A pharmaceutical composition comprising a compound of claim 1, as an active ingredient, in association with a pharmaceutically acceptable, substantially nontoxic carrier or excipient.

* * * * *

UNITED STATES PATENT AND TRADEMARK OFFICE
CERTIFICATE OF CORRECTION

PATENT NO. : 5,670,533
DATED : SEPTEMBER 23, 1997
INVENTOR(S) : MASAAKI MATSUO ET AL

It is certified that error appears in the above-identified patent and that said Letters Patent is hereby corrected as shown below:

Title page, insert --[*] Notice:
--The term of this patent shall not extend beyond the expiration date of Pat. No. 5,134,142--, Signed and Sealed this Twenty-second Day of December, 1998

Attest:

BRUCE LEHMAN

Attesting Officer

Commissioner of Patents and Trademarks